(12) United States Patent
Latta (10) Patent No.: US 12,115,220 B2
(45) Date of Patent: *Oct. 15, 2024

(54) ORAL MUCOSAL CARRIER AND PROTECTANT

(71) Applicant: Inspired Material Solutions, LLC, Omaha, NE (US)

(72) Inventor: Mark A. Latta, Omaha, NE (US)

(73) Assignee: Inspired Material Solutions, LLC, Omaha, NE (US)

( * ) Notice: Subject to any disclaimer, the term of this patent is extended or adjusted under 35 U.S.C. 154(b) by 717 days.

This patent is subject to a terminal disclaimer.

(21) Appl. No.: 17/309,186

(22) PCT Filed: Nov. 5, 2019

(86) PCT No.: PCT/US2019/059853
§ 371 (c)(1),
(2) Date: May 4, 2021

(87) PCT Pub. No.: WO2020/097069
PCT Pub. Date: May 14, 2020

(65) Prior Publication Data
US 2022/0023426 A1    Jan. 27, 2022

Related U.S. Application Data

(60) Provisional application No. 62/755,722, filed on Nov. 5, 2018, provisional application No. 62/846,763, filed on May 13, 2019.

(51) Int. Cl.

| | | |
|---|---|---|
| A61K 36/00 | (2006.01) |
| A61K 9/00 | (2006.01) |
| A61K 31/02 | (2006.01) |
| A61K 31/045 | (2006.01) |
| A61K 31/047 | (2006.01) |
| A61K 31/085 | (2006.01) |
| A61K 31/14 | (2006.01) |
| A61K 31/155 | (2006.01) |
| A61K 31/167 | (2006.01) |
| A61K 31/221 | (2006.01) |
| A61K 31/245 | (2006.01) |
| A61K 31/4164 | (2006.01) |
| A61K 31/4178 | (2006.01) |
| A61K 31/4425 | (2006.01) |
| A61K 31/7036 | (2006.01) |
| A61K 31/714 | (2006.01) |
| A61K 31/717 | (2006.01) |
| A61K 33/00 | (2006.01) |
| A61K 33/06 | (2006.01) |
| A61K 33/16 | (2006.01) |
| A61K 33/30 | (2006.01) |
| A61K 33/40 | (2006.01) |
| A61K 33/42 | (2006.01) |
| A61K 35/644 | (2015.01) |
| A61K 36/185 | (2006.01) |
| A61K 36/28 | (2006.01) |
| A61K 36/484 | (2006.01) |
| A61K 36/537 | (2006.01) |
| A61K 36/889 | (2006.01) |

(Continued)

(52) U.S. Cl.
CPC ............ *A61K 47/34* (2013.01); *A61K 9/006* (2013.01); *A61K 31/02* (2013.01); *A61K 31/045* (2013.01); *A61K 31/047* (2013.01); *A61K 31/085* (2013.01); *A61K 31/14* (2013.01); *A61K 31/155* (2013.01); *A61K 31/167* (2013.01); *A61K 31/221* (2013.01); *A61K 31/245* (2013.01); *A61K 31/4164* (2013.01); *A61K 31/4178* (2013.01); *A61K 31/4425* (2013.01); *A61K 31/7036* (2013.01); *A61K 31/714* (2013.01); *A61K 31/717* (2013.01); *A61K 33/00* (2013.01); *A61K 33/06* (2013.01); *A61K 33/16* (2013.01); *A61K 33/30* (2013.01); *A61K 33/40* (2013.01); *A61K 33/42* (2013.01); *A61K 35/644* (2013.01); *A61K 36/185* (2013.01); *A61K 36/28* (2013.01); *A61K 36/484* (2013.01); *A61K 36/537* (2013.01); *A61K 36/889* (2013.01); *A61K 38/12* (2013.01)

(58) Field of Classification Search
None
See application file for complete search history.

(56) References Cited

U.S. PATENT DOCUMENTS

| | | |
|---|---|---|
| 5,393,745 A | 2/1995 | Schmidt et al. |
| 5,651,959 A | 7/1997 | Hill et al. |

(Continued)

FOREIGN PATENT DOCUMENTS

| | | |
|---|---|---|
| JP | H04-149109 A | 5/1992 |
| JP | 2001-342107 A | 12/2001 |

(Continued)

OTHER PUBLICATIONS

"International Search Report issued in International Application No. PCT/US2019/059853 dated Jan. 27, 2020", Jan. 27, 2020.

(Continued)

*Primary Examiner* — Russell G Fiebig
(74) *Attorney, Agent, or Firm* — Vos-IP, LLC (57) ABSTRACT

An oral mucosal carrier comprising a combination of two different viscosity dimethicone components, wherein the difference between the two different viscosity dimethicone components is about 2.0 million cP or greater; and comprising at least one active agent.

20 Claims, 3 Drawing Sheets

(51) Int. Cl.
*A61K 38/12* (2006.01)
*A61K 47/34* (2017.01)

(56) References Cited

U.S. PATENT DOCUMENTS

| | | |
|---|---|---|
| 7,264,882 B2 | 9/2007 | Engelbrecht |
| 7,858,570 B2 | 12/2010 | Hare |
| 8,603,550 B1 * | 12/2013 | Fusco .................. A61K 8/9789 424/725 |
| 9,566,226 B2 | 2/2017 | Midha et al. |
| 9,968,101 B2 | 5/2018 | Modak et al. |
| 10,028,919 B2 | 7/2018 | Kaufman |
| 2004/0033205 A1 | 2/2004 | Date et al. |
| 2004/0167479 A1 | 8/2004 | Warren et al. |
| 2012/0237464 A1 | 9/2012 | Ahn et al. |
| 2014/0105941 A1 | 4/2014 | Mchale et al. |
| 2015/0366786 A1 | 12/2015 | Huo et al. |
| 2016/0106659 A1 | 4/2016 | Lamberty et al. |
| 2017/0281520 A1 * | 10/2017 | El-Khouri .............. A61K 8/891 |
| 2018/0207213 A1 * | 7/2018 | Mcelvany .............. A61K 8/922 |

FOREIGN PATENT DOCUMENTS

| | | |
|---|---|---|
| WO | WO/2001/001940 A1 | 1/2001 |
| WO | WO/2012/144943 A1 | 10/2012 |
| WO | WO/2014/059143 A1 | 4/2014 |
| WO | WO/2017/173267 A1 | 10/2017 |
| WO | WO/2018/075018 A1 | 4/2018 |
| WO | WO/2018/165078 A1 | 9/2018 |

OTHER PUBLICATIONS

"Polydimethylsiloxane", Wikipedia, Oct. 12, 2018, https://en.wikipedia.org/w/index.php?title=Polydimethylsiloxane&oldid=863655868.

* cited by examiner

ORAL MUCOSAL CARRIER AND PROTECTANT

CROSS-REFERENCE TO RELATED APPLICATIONS

This application is a 371 National Phase Entry of International Patent Application No. PCT/US2019/059853 filed on Nov. 5, 2019, which claims the benefit of U.S. Provisional Application No. 62/755,722 filed on Nov. 5, 2018, and U.S. Provisional Application No. 62/846,763 filed on May 13, 2019, the contents of each of which are incorporated herein by reference in their entirety.

FIELD OF INVENTION

The present invention is generally related to oral mucosal carriers and protectants, suitable for oral use, and particularly for providing an additive or therapeutic to the oral mucosa, comprising at least two different viscosity dimethicone components and at least one excipient for application to the oral mucosa.

BACKGROUND OF THE INVENTION

Oral-based care products, including mouthwashes, prophy pastes, gels, toothpastes, lozenges, and the like are sold to meet a diversity of patient needs. Toothpastes are one of the most common oral care products and are specifically utilized to reduce and prevent caries through brushing on the gel or paste, which comprises fluoride and other components. These products are frequently sold in an over-the-counter strength and are used throughout the world for their protective and reparative properties.

While toothpastes are ubiquitous, other oral care products are necessary to meet patient needs, including those for treatment with orthodontic brackets, dry mouth, halitosis treatment, canker sore, tooth hypersensitivity, dry socket treatments, whitening, and care of the oral mucosa for lacerations, bleeding, cuts, sores, fungal, viral, and bacterial infections, sun damage, skin damage, and for cancerous growths. These products come in many different forms including: sprays containing an active ingredient, while other products include lozenges, foams, gels, pastes, or other materials for oral application. Unfortunately, many of these products are agents that temporarily address or mask an issue, without actually treating the cause of the disease or issue faced by the patient.

Treatment of the oral mucosa has the ability to impact a wide variety of problematic issues and new products are needed that provide for a carrier having sufficient properties for use in treating these afflictions of the oral mucosa. Accordingly, the creation of new products is necessary to create safe, reliable, and highly efficacious products for oral mucosal treatment and application.

SUMMARY OF THE INVENTION

In a preferred embodiment, an oral mucosal carrier comprises a first and second dimethicone, said first dimethicone having a viscosity between 1,000 and 25,000 cP, and a second dimethicone having a viscosity of between 2.0 million cP and 3.0 million cP; and an active agent, suitable for oral application. In a preferred embodiment, the active agent is selected from the group consisting of: a fluoride donor, a calcium donor, a phosphate donor, an antimicrobial agent, and combinations thereof.

An oral mucosal carrier comprising between 25-99% of a 12,500 cP dimethicone and between 1% and 50% of a 2.5 million cP dimethicone; and a 0.1%-1.5% fluoride donor, antimicrobial agent, or combinations thereof.

An oral mucosal carrier comprising between 25-99% of a 1,000 cP dimethicone and between 1% and 75% of a 2.5 million cP dimethicone; and a 0.1%-1.5% sodium fluoride, benzalkonium chloride, or combinations thereof.

In certain embodiments, there is concentration of a fluoride donor between 800 and 1500 ppm fluoride, as allowable under FDA regulations for over the counter applications. In a preferred embodiment, the concentration of the fluoride agent derives a concentration of about 1000 ppm fluoride or about 1100 ppm fluoride. In certain embodiments, a 1000 ppm fluoride is derived by incorporating a concentration of about 0.4% stannous fluoride, about 0.22% of sodium fluoride, and about 0.76% of sodium monofluorophosphate. In certain embodiments, a 1100 ppm fluoride is derived by incorporating a concentration of about 0.454% stannous fluoride, about 0.243% sodium fluoride, or about 0.836% sodium monofluorophosphate. In certain applications, prescription strength materials may be provided with concentrations of 5000 ppm or less. In certain embodiments the fluoride donor is selected from the group consisting of: sodium fluoride, stannous fluoride, sodium monofluorophosphate, ACPF (amorphous calcium phosphate fluoride), amine fluoride 297, and combinations thereof.

An oral mucosal carrier comprising two dimethicone polymers, and a fluoride; a first dimethicone polymer having a formula of $Me_3$-O—[$SiMed_2$]n-$Me_3$ wherein "n" is a number of repeating units, having a viscosity of between about 1,000 and 25,000 cP, and a second dimethicone polymer having a formula wherein n is larger than the first dimethicone polymer, and having a thicker viscosity of between about 2.0 million cP and 3.0 million cP; with the first dimethicone polymer comprising between 10 and 99 percent of the total mass of the formulation and said second dimethicone polymer comprising between 1 and 90 percent of the total mass of the formulation.

An oral mucosal carrier comprising two dimethicone polymers, and a fluoride; a first dimethicone polymer having a formula of $Me_3$-O—[$SiMe_2$]n-$Me_3$ with "n" repeating units, and a second dimethicone polymer having a greater viscosity and more "n" repeating units than the first dimethicone polymer; with the first dimethicone polymer in a ratio with the second dimethicone polymer of between 100:1 to 1:8. Preferably the ratio is between about 50:1 to about 1:2, or about 40:1 to about 1:1.

A method of formulating an oral mucosal carrier comprising a first and second dimethicone comprising: adding an amount of a first dimethicone, said first dimethicone having a lower viscosity than said second dimethicone, to a centrifugal mixer; adding to said first dimethicone an amount of at least one excipient and mixing said first dimethicone with said at least one excipient in said centrifugal mixer; adding to the mixed first dimethicone and said at least one excipient an amount of said second dimethicone and mixing said resulting material in said centrifugal mixer. In certain embodiments, the second dimethicone is admixed into the first dimethicone in at least two portions, a first portion and a second portion. Said first and second portion may be equal amounts or unequal amounts. In certain embodiments, said second dimethicone is admixed in 2, 3, 4, 5, 6, 7, 8, 9, 10, or more portions, wherein between each additional amount of said second dimethicone, the mixture is mixed in said centrifugal mixer.

In certain embodiments, the active ingredient is selected from the group consisting of: antibiotic materials, Sulphur compounds, skin healing compounds, bone growth promoting compounds, antimicrobial agents, topical anesthetic, antifungal, $CoQ_{10}$, vitamin D, chlorhexidine, FDA monographed compounds identified at the Web address https://www.fda.gov/downloads/AboutFDA/CentersOffices/CDER/UCM135688.pdf, chitosan, hemostatic materials, anti-inflammatory, topical steroid, anti-inflammatory compounds, hemp-based extracts including cannabinoids and terpenes including but not limited to THC and CBD, silver nitrate, essential oils, skin protectant agents, pain relief or blocking agents, zinc oxide, small molecules, nitroglycerin, nicotine, hormones, or combinations thereof.

In one embodiment, the oral mucosal carrier further comprising a phosphate donor, wherein said phosphate donor is selected from the group consisting of: potassium phosphate monobasic, potassium phosphate dibasic, dicalcium phosphate, tricalcium phosphate, sodium phosphate monobasic, sodium phosphate dibasic, monomagnesium phosphate, dimagnesium phosphate, and combinations thereof.

In one embodiment, the oral mucosal carrier further comprising a calcium donor selected from the group consisting of: calcium nitrate, calcium chloride, calcium citrate, calcium sulfate, calcium oxalate, calcium fluoride, dicalcium phosphate, tricalcium phosphate, calcium gluconate, and combinations thereof. In a further embodiment, the calcium donor may further include at least one amino acid. In a further embodiment, wherein the amino acid is lysine.

In one embodiment, the oral mucosal carrier further comprising a potassium donor selected from the group consisting of: potassium nitrate, potassium chloride, potassium phosphate monobasic, potassium phosphate dibasic, and combinations thereof.

In one embodiment, the oral mucosal carrier further comprising a flavorant or a sweetener selected from the group consisting of: spearmint oil, wintergreen oil, peppermint oil, bubblegum, cherry, vanilla, chlorophyll, acesulfame K, sucralose, xylitol, saccharin, sodium cyclamate, and combinations thereof.

In one embodiment, the oral mucosal carrier further comprising an antimicrobial agent selected from the group consisting of: benzalkonium chloride, cetylpyridinium chloride, trans-farnesol, chitosan, chlorhexidine, quaternary ammonium compounds, phenols, bisguanides, and combinations thereof.

In one embodiment, the oral mucosal carrier further comprising one or more of a bulking agent, a flowing agent, a preservative, or combinations thereof. As with the inclusion of a flavorant, it may be suitable to provide a small amount of a bulking agent or texturizing agent to the product to impart a tactile feel to the material, or to improve its consistency for application to the tooth surfaces. For example, patients may prefer to have a slight texture on the material to allow for a patient to "feel" like the material remains on the surfaces of the oral mucosa. Bulking agents may be necessary to simply provide for a superior consistency and overall feel to the product. A flowing agent or glidant may similarly be added to the compositions herein to impart modify the physical properties of the material. For example, magnesium stearate, stearic acid, silicon dioxide, glycerin, palmitate, and others known to those of ordinary skill in the art.

In one embodiment, the oral mucosal carrier further comprising one or more of a whitening agents selected from the group consisting of: urea peroxide, calcium peroxide either alone or in combination with amino acids such as L-lysine, titanium dioxide, hydrogen peroxide, and complexes of polyvinylpyridine (PVP), hydrogen peroxide, and combinations thereof.

In a preferred embodiment, a dimethicone-based oral mucosal carrier comprising a first dimethicone material having a viscosity of between about 1,000 cP and 25,000 cP, and a second dimethicone material having a viscosity of between about 2.0 million and 3.0 million cP; and at least one active agent. In a preferred embodiment, wherein the at least one active agent is selected from the group consisting of: a fluoride donor, cetyl pyridinium chloride, benzalkonium chloride, and combinations thereof. In a preferred embodiment, wherein the fluoride donor is selected from the group consisting of sodium fluoride, stannous fluoride, ACPF, and combinations thereof. In a preferred embodiment, the carrier wherein the ratio of the first dimethicone to the second dimethicone is between 100:1 and 1:10; 50:1 and 1:2; or 40:1 and 1:1. In a preferred embodiment, the oral mucosal carrier wherein the concentration of the fluoride donor is between 0.1 and 1.5%; or wherein the concentration of the fluoride donor is between 1 and 1500 ppm, or more particularly between 800 ppm and 1500 ppm. In a preferred embodiment, the oral mucosal carrier further comprising a calcium donor. In a further preferred embodiment, the oral mucosal carrier further comprising a potassium donor. In a further preferred embodiment, the oral mucosal carrier further comprising a flavorant or a sweetener. In a further preferred embodiment, the oral mucosal carrier further comprising cetyl pyridinium chloride. In a further preferred embodiment, the oral mucosal carrier further comprising a bulking agent, a flowing agent, a preservative, or combinations thereof. In a further preferred embodiment, the oral mucosal carrier further comprising a phosphate donor.

In a further preferred embodiment, a method of formulating the oral mucosal carrier comprising a first and second dimethicone materials; comprising placing the entirety of the first dimethicone component into a mixing container and adding into it an amount of an active ingredient; mixing the two components at 3,000 RPM for about 10 minutes in a centrifugal mixer, after mixing for 10 minutes, adding to the now mixed material a portion of the second dimethicone, wherein one fifth of the total concentration of the second dimethicone is added in separate increments and mixing the resulting material at 3,000 RPM for five minute increments before adding another incremental portion of the second dimethicone, until all of the second dimethicone is added and admixed into the oral mucosal carrier.

In a preferred embodiment, the method comprising adding a calcium donor with the first dimethicone and the active agent before mixing the components. In a preferred embodiment, the method comprising adding a fluoride, calcium, potassium donor, cetyl pyridinium, chloride, or combinations thereof, with the first dimethicone and fluoride before mixing the components. In a further preferred embodiment, the method comprising adding a benzalkonium chloride or cetyl pyridinium chloride with the first dimethicone before mixing the components.

In a further preferred embodiment, an oral mucosal carrier composition consisting essentially of: a dimethicone-based oral mucosal carrier comprising a first dimethicone material having a viscosity of between about 1,000 cP and 25,000 cP, and a second dimethicone material having a viscosity of between about 2.0 million and 3.0 million cP; and at least one active agent. In a further embodiment, the composition wherein the first dimethicone to the second dimethicone is combined in a ratio between 100:1 and 1:10. In a further embodiment, the composition wherein the composition consisting essentially of at least one active agent.

In a further preferred embodiment, the oral mucosal carrier wherein the active agent is a therapeutic agent selected from the group consisting of: sodium fluoride, difluorosilane, stannous fluoride, APF (acidulated phosphate fluoride) ACPF (amorphous calcium phosphate fluoride), ACP (Amorphous calcium phosphate), sodium monofluorophosphate, benzalkonium chloride, potassium phosphate dibasic, calcium nitrate, cetylpyridinium chloride, phosphate donors, potassium donors as well as antibacterial, antifungal, antiviral, small molecules, antiemetic materials, biologic materials, self-replicating peptides, cannabinoids, terpenes, and combinations thereof. In a further embodiment, wherein the active agent is a hemp extract.

In a further embodiment, the therapeutic agent may be selected from a dry mouth treating agent selected from the group consisting of: pilocarpine, acetylcholine, electrolytes such as sodium, potassium, calcium, magnesium, chloride, phosphate, and carbonates. In a further embodiment, the therapeutic agent may be a saliva enhancer selected from the group consisting of: essential oil extracts, spilanthes, xylitol, carboxymethylcellulose and variations of the same to enhance saliva flow. In a further embodiment, the therapeutic agent is a halitosis treatment agent selected from the group consisting of: an antibacterial compound, a natural or synthetic oil, an odor destroying agent, or an odor masking agents.

In a further embodiment, the composition for a canker sore treatment, wherein the therapeutic agent is a Canker sore treating agent selected from the group consisting of: Alum powder (potassium aluminum sulfate), baking soda, probiotics, honey, coconut oils or other natural oil having antimicrobial properties, magnesium hydroxide, chamomile, echinacea, sage, deglycyrrhizinated licorice (DGL), zinc, Vitamin $B_{12}$, antimicrobial compounds, and combinations thereof.

In a further embodiment, the composition is a dry socket treatment, wherein the therapeutic agent is a Dry Socket Treatment agent selected from the group consisting of: a pain relief agent, an antibacterial agent, a tissue growth agent. In a further embodiment, wherein the therapeutic agent is selected from the group consisting of: NSAID, opioid, acetaminophen, chlorhexidine, metronidazole, guaiacol, eugenol, balsam of Peru, chlorobutanol, iodoform, butamben, polymyxin B sulfate, tyrothricin, neomycin sulfate, tetracaine hydrochloride, and combinations thereof.

In a further embodiment, wherein the composition has whitening agents, specifically, wherein the therapeutic agent is a peroxide.

Use of the oral mucosal carrier of any embodiment herein to treat an oral fungal, bacterial, or viral infection.

DETAILED DESCRIPTION OF THE INVENTION

The oral mucosa is constantly attacked by sugars, alcohols, low and high pH foods and beverages, and materials that stain or damage tooth, enamel, and the gums of individuals. Fortunately, as described herein an oral mucosal carrier product creates a useful material for several ailments of the oral mucosa. Included among the ailments are treatment of tooth surfaces, for example for prevention of caries and for reduction of tooth sensitivity. However, the oral mucosa is more than just teeth and gums, and many individuals face afflictions that are painful, uncomfortable, or embarrassing, that require treatment with certain active or inactive ingredients.

For example, treatment of orthodontic tooth surfaces is necessary, as many times, before application of a cement to the tooth, the tooth is etched to enable a better and more secure attachment for the bracket. Etching is simply removing a layer of dentin or enamel from the tooth surface and may create sensitivity or access to the tooth, if not treated. Accordingly, after a tooth is treated for orthodontics, a material capable of being applied around the bracket, and onto the tooth surfaces and into the oral mucosa may assist in remineralizing the tooth surface to repair any damage that may have incidentally occurred.

Many individuals also suffer from dry mouth. Dry mouth occurs to individuals suffering from allergies, may occur simply with aging, may occur due to occupational activities, due to ambient relative humidity, presence of pollutants in the air, due to medical treatments, or due to other social endeavors. For example, those who utilize certain cannabinoid products often complain of a side effect of dry mouth, despite the relief provided by the medication. As described herein, the oral mucosal carrier provides a barrier while providing a lubricating tactile feel and delivery of an excipient or another therapeutic to provide relief for any number of oral care needs.

A large percentage of the population also suffers from halitosis. Those who suffer may have secondary medical concerns, include those brought on by sleep apnea or snoring, but also those who have trouble breathing through their nose, or simply through an accumulation of bacteria in the oral mucosa that leads to the halitosis. Treatment is frequently through better care habits, including brushing and flossing, but also through use of certain oral mouthwashes, which far too often simply mask the issue for a short period of time.

Many individuals also face a burden from the formation of canker sores, or from other mouth sores that form from overuse, misuse, or progression of viral or bacterial diseases. Canker sores are particular frustrating as they seemingly form from nowhere and provide painful open sores for several days. Existing technology typically coats the open sore to promote healing, often with a material such as with a cyanoacrylate. However, the formulation of the present embodiments can further treat aphthous ulcers and other mouth sores including sores from lichen planus, stomatitis, and herpes. New formulations having protective properties are welcomed in this field, to better treat canker sores as well as other mouth and oral sores.

Tooth hypersensitivity is a critical issue for those who suffer from dentin removal or recession of the gum, to reveal tubules in the tooth surface that lead to nerve endings in the mouth. Such hypersensitivity makes eating or drinking painful as many materials will cause discomfort for the individual. Materials that will both treat the underlying issue, typically from gum disease or from damage to the tooth surface, as well as protective barrier, can dramatically alter the treatment options for patients who suffer from hypersensitivity.

Dry socket (alveolar osteitis) occurs fairly often after tooth extraction procedures. While modern dental practices seek to prevent extraction, there are times when the extraction is necessary to prevent further pain, discomfort, or to alleviate damaged or diseased tissues. Dry socket occurs when the blood clot that forms after a tooth extraction is released and the bone inside the socket becomes exposed. Treatment is frequently provided by flushing with saltwater and packing the wound with gauze, gelatin, or with another sealant. Clove oil, or other antiseptic material is frequently added to prevent bacterial infection and to sooth the open wound. Once pain has subsided, the wound heals on its own. However, such issue is better treated with an oral carrier that is mucoadhesive and can form a better barrier and provide relief to the specific injury site.

Oral Thrush or oral candidiasis is caused by the fungus *Candida albicans*, which accumulates in the lining of the mouth. While this is a normal organism in the mouth, at times, the oral mucosa allows for overgrowth and leads to discomfort, typically in infants and toddlers. Therapeutic treatment with the oral carrier and an antifungal, provides a quick and efficient method for control of this discomfort and elimination of fungal infection.

Whitening of tooth surfaces is often provided by peroxides, which effectively bleach the tooth surface to remove stains. The present embodiments provide for an improved mucoadhesive material that will increase retention time and contact with the tooth surfaces to increase the efficiency of the peroxide and whitening agents.

Indeed, each of these issues, alone, are significant issues faced by both individuals and by dental professionals treating the individuals. The ability to reduce caries, reduce dentin sensitivity, treat dry mouth, halitosis, canker sores, fungal, viral, or bacterial sores, as well as dry socket concerns would be invaluable. Indeed, these afflictions are faced by a wide range of patients, including children with immature teeth and include children and adults with mature teeth.

A common theme with many oral mucosal concerns is providing two features: first a protectant, to protect the area of concern from the mouth itself, whether it be from hot or cold foods, sugar, salt, or materials ingested, or from the tongue touching surfaces within the mouth, or simply from discomfort due to the affliction, a material that provides a coating and barrier protection to the oral mucosa will provide immediate and lasting relief for many afflictions. At the same time, something that simply protects or provides a coating may either reduce the ability of the body to heal, or, it would prevent entry of other products to the oral mucosa that may provide therapeutic relief for the individual. Here, embodiments are directed towards an oral mucosal carrier and protectant product that provides a carrier and reservoir for an excipient or therapeutic for treatment of the affliction as well as a barrier material to provide skin protection inside of the oral mucosa.

Figure 1:
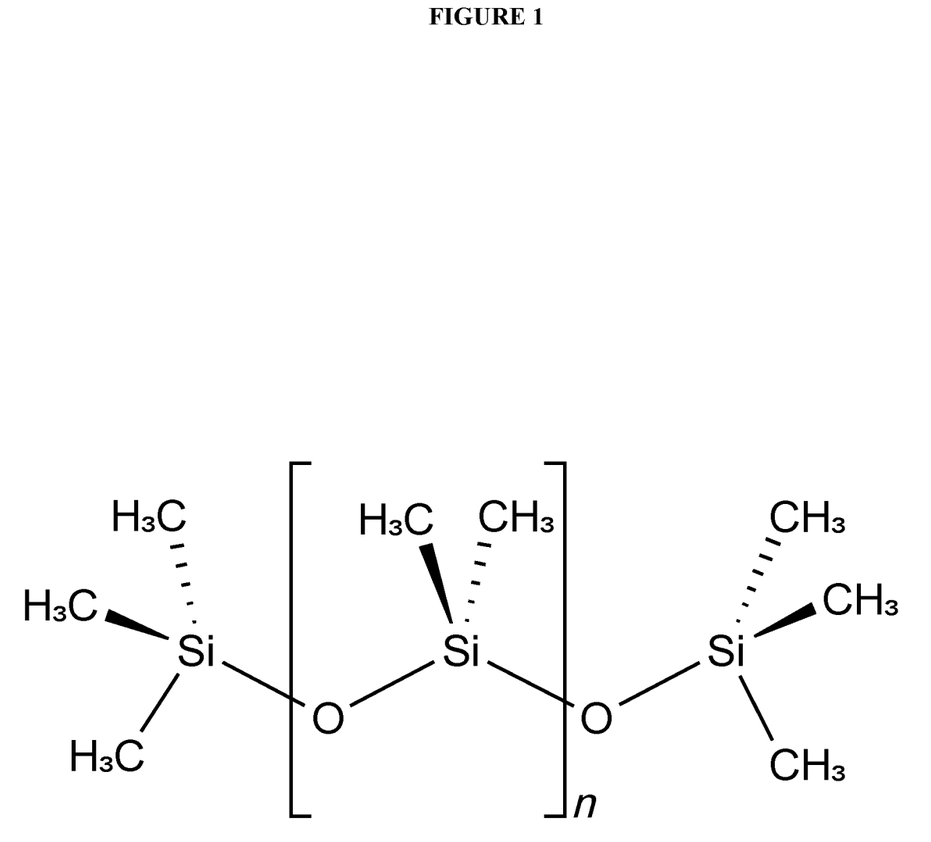
FIG. 1 depicts a figure of the formula of PDMS (Dimethicone) having n number of repeating siloxane units.

The oral mucosal carrier and protectant comprises a first dimethicone product having a first viscosity. FIG. 1 details a generic formula for dimethicone, with "n" number of repeating units. The greater the number of repeating "n" units, the greater the viscosity of the material. The oral mucosal carrier and protectant further comprises a second dimethicone product, having a second viscosity, wherein the second dimethicone product's viscosity is at least 2.0 million cP greater than the viscosity of the first dimethicone product, and preferably at least 2.1, 2.2, 2.3, 2.4, or 2.5 million cP greater viscosity that the first dimethicone product. In certain embodiments the difference is between 2.5 and 3.0 million cP. The cP unit (centipoise) is a unit of dynamic viscosity. The combination of the two viscosities provides a material that provides for a physical barrier by forming a layer that mucoadheres to the tooth surface or oral mucosa, wherein the material, once coated onto a tooth surface or mucosal surfaces, is resistant to being removed through a strong adhesion. This material, accordingly, forms a barrier of this coating on tooth surfaces and the oral mucosa. However, it also serves as a reservoir for excipients or therapeutics for treatment of one or of many of the afflictions described herein.

For example, the oral mucosal carrier and protectant may be in the form of a paste, a gel, a foam, an aerosol, a liquid, or be provided as a food material, such as a lozenge or a gummy. Each of these forms allows application into the mouth, wherein the oral mucosal carrier coats the surface of the oral mucosa. Thereafter, the materials admixed into the dimethicone are released into the oral mucosa or onto tooth surfaces where the efficacy of such products can allow for treatment of the oral mucosa.

The embodiments of the present disclosure detail a carrier material that is free from rosin, does not require the use of an alcohol as a solvent, and is aqueous free. Indeed, the ability to remove the rosin and the solvent provides for new products for those who are allergic to rosin, or those sensitive to the alcohol residuals from existing products. The embodiments herein allow for formation of a carrier that is highly adhesive to tooth and oral mucosal surfaces and allows for carrying of active agents to precipitate onto tooth surfaces.

As used herein, the term active agent, additive, and excipient are used interchangeably to mean any material added to the carrier product of the present embodiments other than the dimethicone components. This term includes additional excipients and therapeutic agents, and including, but not limited to: flavorants, colorants, binders, bulking agents, preservatives, alcohols, titanium dioxide, sweetener, dimethacrylates, waxes, fats, oils, Gantrez® (synthetic, alternating copolymers of methyl vinyl ether [MVE] and maleic anhydride), flowing agents, stabilizers, saliva enhancers, etc.

As used herein, the term therapeutic agent or therapeutic compound means, a material which provide a medicinal, healing, or therapeutic effect to at least one cell in the oral mucosa as understood by those of skill in the art. Nonlimiting examples include: certain fluoride or calcium donors, sodium fluoride, difluorosilane, stannous fluoride, APF (acidulated phosphate fluoride) ACPF (amorphous calcium phosphate fluoride), ACP (Amorphous calcium phosphate), sodium monofluorophosphate, benzalkonium chloride, potassium phosphate dibasic, calcium compounds, calcium nitrate, cetylpyridinium chloride, phosphate donors, potassium donors as well as antibacterial, antifungal, antiviral, antibiotic agents, small molecules, antiemetic, biologic materials, self-replicating peptides, cannabinoids, terpenes, and combinations thereof.

Components of Oral Mucosal Carrier of the Present Disclosure

Dimethicone, also known as polydimethylsiloxane or PDMS is a silicone-based polymer of varying size, based on the number of repeating units of the polymer. Dimethicones have wide ranging uses, for example in antiperspirants, skin creams, skin lotions, suntan lotions, bath oils, hair care products, and as coatings for oral products. Skin care products have a wide range of uses and dimethicone is relied upon for its properties as a base for a wide range of cosmetic formulations, its hydrophobicity, range of viscosities, lubricating properties, low surface tensions, clear, tasteless, odorless, inert, and that it is miscible with a wide range of other materials.

Indeed, dimethicones of various viscosity are relied upon in many cosmetic formulations where it is used for filling in uneven texture and fine lines, such as in primers, foundations, or lotions. Furthermore, as a silicone oil, it provides a protective cover on skin such as with suntan lotions or other skin lotions.

Dimethicones are also used in hair care products, to provide smoothness, specifically in conditioners or detangling products. Indeed, the incorporation of dimethicone into said products assists with smoothing hair and providing ease for reducing or removing knots in hair. Furthermore, in many hair care products, dimethicones are utilized to leave a shine or sheen on hair. This is due to the product coating the hair and leaving a small layer of the material on the hair itself.

PDMS has the typical formula:

with the number of "n" repeating units impacting the viscosity of the material. Dimethicone products are often sold in various formulations by their viscosity. Here, we combine at least two different viscosity dimethicone, one preferably having a viscosity of between about 1,000 cP and 25,000 cP and a second preferably having a viscosity of between about 2.0 million cP and 3.0 million cP, and most preferably between about 2.1 and 2.9, or 2.2 and 2.8, or 2.3 and 2.7, or 2.4 and 2.6 or most preferably about 2.5 million cP. When purchasing these materials, a typical certificate of analysis will provide a viscosity as determined by a rotational test, and each certificate of analysis will provide a specification limit for the material, usually within about 10%, or about 5%, or about 1% of a stated specification. For example, for a stated material having a 2.5 million cP viscosity, the materials used in the embodiments herein comprised a specification range of 2,312,500 to 2,687,500 cP.

The FDA has approved dimethicone for personal care products and the material is generally considered safe for use. Indeed, the FDA lists at least 16 entries for topical, transdermal, and oral applications for dimethicone. Of these, four are specifically listed for oral applications, namely dimethicone 100, 350, 350, and 1000, with the duplicate 350 entries being one for a capsule and the other for a "capsule, sustained action." Accordingly, dimethicones have a known and expected safety profile with the FDA.

The difference in viscosity for dimethicone comes simply in the number of repeating polymer units of the molecule. For example, a polymer having a greater number of repeating units will tend to restrict movement of the polymer and thus will have a greater viscosity than one with a lower number of repeating units. However, when purchasing these dimethicone products commercially, in nearly every example, the materials are sold by their viscosity, with a range or variation of about 1-10% of the stated viscosity.

In creating a formulation for the present oral mucosal carrier products, we needed to confirm all of the above considerations, namely: rate or release of active ingredients, adhesive forces, as well as the aesthetic and tactile response of the material to generate a superior product. As detailed in Formulations 1-9 below and in Table 3, we tested several different basic formulations, one using a 1,000 cP component with the 2.5 million cP dimethicone, and a second where the 1,000 cP dimethicone was replaced with a 12,500 dimethicone. We also tested variations using a 25,000, 50,000 cP, and 100,000 cP mixed with the 2.5 million dimethicone. Finally, we tested the 1,000 and 12,500 dimethicones with a lower 1.5 million cP dimethicone so as to evaluate the material in different concentrations and with different base materials.

In summary, compositions comprising a first dimethicone with a viscosity of less than 50,000 cP was more effective than those of 50,000 cP or greater, regardless of whether a 1.5, 2.0, 2.5 or 3.0 million cP viscosity second dimethicone was utilized. Furthermore, the difference in viscosity also appeared to be important, up to a point, namely that those using the 2.5 cP dimethicones functioned better than those mixed with the 1.5 million cP product. However, this is not to say that the 50,000 cP material, as the lower viscosity dimethicone, was not significantly superior than the materials that are presently available. Accordingly, in the broadest sense, the combination of the two dimethicone materials, of varying viscosity, provides for significant advantages.

In a preferred embodiment, a first dimethicone of between 1,000 cP and 50,000 cP, and optimally between 1,000 cP and 25,000 cP is admixed with a second dimethicone of 2.5 million cP and resulted in optimal retention and adhesion to the oral mucosa while also allowing for an appropriate feel, physical properties, and release profile.

In a preferred embodiment, an oral mucosal carrier composition consisting of a dimethicone-based oral mucosal carrier comprising a first dimethicone material having a viscosity of between about 1,000 cP and 25,000 cP, and a second dimethicone material having a viscosity of between about 2.0 million and 3.0 million cP; and at least one active agent.

In a further preferred embodiment, the composition wherein the first dimethicone to the second dimethicone is combined in a ratio between 100:1 and 1:10. In a further preferred embodiment, wherein the composition comprises two or more active agent. In a further preferred embodiment, the composition comprising at least one therapeutic agent.

In a further preferred embodiment, the composition wherein the active agent is a bulking agent. In a further preferred embodiment, wherein the bulking agent is an edible wax. In a further preferred embodiment, wherein the bulking agent comprises between 0.01 and 15% of the total weight of the composition.

In a further preferred embodiment, the composition wherein the active agent is a therapeutic agent selected from the group consisting of: sodium fluoride, difluorosilane, stannous fluoride, APF (acidulated phosphate fluoride) ACPF (amorphous calcium phosphate fluoride), ACP (Amorphous calcium phosphate), sodium monofluorophosphate, benzalkonium chloride, potassium phosphate dibasic, calcium nitrate, cetylpyridinium chloride, phosphate donors, potassium donors as well as antibacterial, antifungal, antiviral, antibiotic agents, small molecules, antiemetic, biologic materials, self-replicating peptides, cannabinoids, terpenes, and combinations thereof. In a further preferred embodiment, the composition wherein the active agent is a hemp extract.

Formulation of a Product for Oral Mucosal Carrier Use

In creating an oral formulation, typically, the formulation includes more than just the carrier, and specifically includes an active ingredient. In further embodiments, the carrier and active ingredient are further combined with one or more excipients, which are typically added to generate a particular formulation, or to improve the formulation, its consistency, viscosity, texture, taste, feel, or to incorporate inclusion of other active ingredients for oral treatment.

A primary use of these oral mucosal carrier and protectant materials is for tooth remineralization. For example, orthodontic bracket treatments, as previously described, may require some etching or damage to tooth enamel surfaces. Thus, after a bracket is adhered, treatment of the tooth surface would be advantageous to aid in remineralization and to prevent sensitivity or caries due to the weakening or removal of the enamel surface for the orthodontic application of brackets. An over the counter strength, i.e. at less than 1,500 ppm, may be suitable for long-term use, however a 5,000 ppm concentration may also be appropriate for application under prescription, at a dental office, which can order the higher ppm concentration by prescription. Application of such a material is typically through a liquid, paste, foam, or gel like application to the tooth surface, or adjacent to the bracket as placed on the tooth surface. Studies have confirmed that the high concentration of fluoride is shown to dramatically prevent the incidence of caries for both immature and mature tooth surfaces when fluoride is applied at a dental visit.

For example, a prescription strength fluoride oral mucosal carrier and protectant product is painted onto or applied via any number of different applications, and paint or coat each tooth surface and remains in place for usually about 1 to 8 hours, with a typical treatment having the product on the tooth surface for between 4 to 6 hours. Eating and drinking a limited diet is acceptable directly after application but brushing of the tooth surfaces or other food or drink materials that rub the tooth surfaces will prematurely remove some of the product from the tooth surface.

This product is unlike existing fluoride products that frequently utilize a natural resin, which dries with a yellow or brown like coloration that is problematic for most users because of cosmetic appearances, and it also eliminates or reduces the uncomfortable taste and texture for the resin-based fluoride products. Indeed, the oral mucosal carrier and protectant described herein leaves a smooth coating on tooth surfaces and can be flavored with any number of flavorants. Specifically, this product excludes rosin, and thus also excludes the alcohol solvent that is required for rosin-based products.

Figure 2:
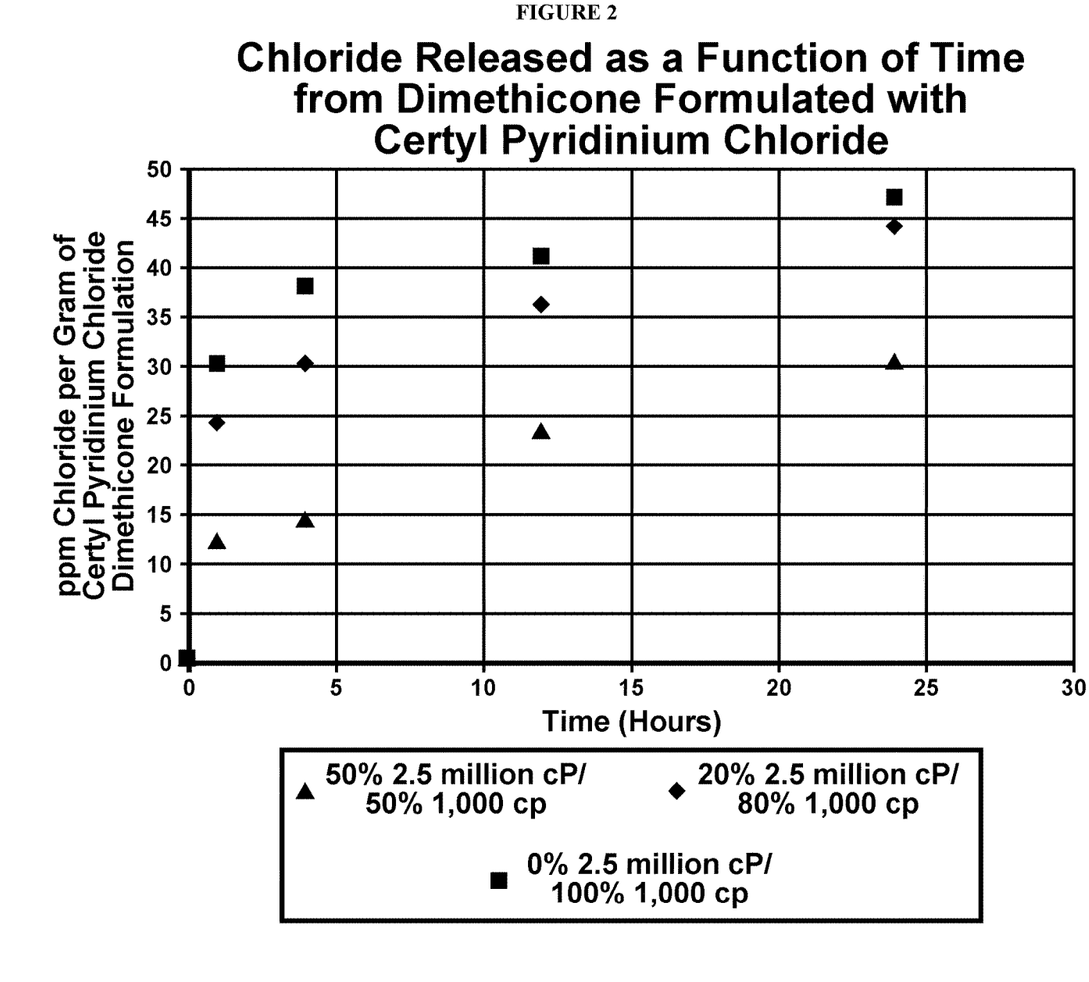
FIG. 2 depicts a release profile of several different blends of the present disclosure, with regard to release a therapeutic such as cetyl pyridinium chloride over a 24-hour period.

Oral mucosal carriers of the present embodiments are developed to adhere to oral mucosal surfaces, where the material itself serves as a reservoir for therapeutics, such as cetyl pyridinium chloride, to allow for desired antimicrobial activity in the oral environment. Indeed, as depicted in FIG. 2, the graph provides values for release of chloride from the cetyl pyridinium chloride material based upon three different formulations, one having 1:1 ratio of 2.5 million cP and 1,000 cP dimethicone, a second having 1:4 ratio of 2.5 million and 1,000 cP dimethicone, and a third at 100% 1,000 cP dimethicone. Time and release profile are both instrumental in allowing the chloride to leave the carrier and to allow for release of therapeutics to mucosal surfaces.

Table 3, below, details several different formulations of the present disclosure, each having a different amount of forces (peak adhesive forces) and (total work of adhesion) which provide for a value of each material with respect to its adhesive forces. Those with a greater adhesion are going to typically remain on a mucosal surface for a greater period of time than one with a lower peak adhesive force. Accordingly, formulations using a higher percentage of the higher viscosity dimethicone had a greater adhesive property as compared to those using a lower percentage of the higher viscosity dimethicone.

At the same time, there must be a balance between the peak adhesive forces and the rate of dissolution of the agent, which, in FIG. 2 is chloride. FIG. 2 provides that those with higher amounts of the 2.5 million cP dimethicone have a slower dissolution rate of the chloride from the carrier. At a 1:1 ratio of the two dimethicone materials, the chloride release rate is nearly one half of that with the other two tested release profiles of the present disclosure. Accordingly, while the product with only the 1,000 cP dimethicone had the fastest release profile from 0-5 hours, at 24 hours, its total release was nearly identical to that of the 4:1 (low viscosity:high viscosity dimethicone) ratio product. And, the 4:1 ratio product has a dramatic and significant improvement in adhesion than the 1,000 cP material. Accordingly, an effective release to the oral mucosa will be much higher using the materials having the 2.5 million cP dimethicone, as they will be retained on the oral mucosa for a longer duration than those without the high viscosity dimethicone.

At 24 hours, the release profile of the 1:1 ratio product reached over 40 ppm chloride per gram of the carrier. The importance of these release profiles is to evaluate the two-fold concern of a release rate that allows for uptake of the released chloride, while balancing the need for adhesion to maintain the material on an oral mucosa surface. For example, if the 1,000 cP material alone washes off the oral mucosal surface in 30 minutes, its fast rate of release is not sufficient because it would not have sufficient time to allow for release of the therapeutic. Similarly, too fast of a release may simply release materials into the saliva and not allow for sufficient uptake of the therapeutic to the oral mucosal tissues. Thus, a slightly slower release may benefit and ultimately exceed a fast release, when considering the oral mucosal surface.

Figure 3:
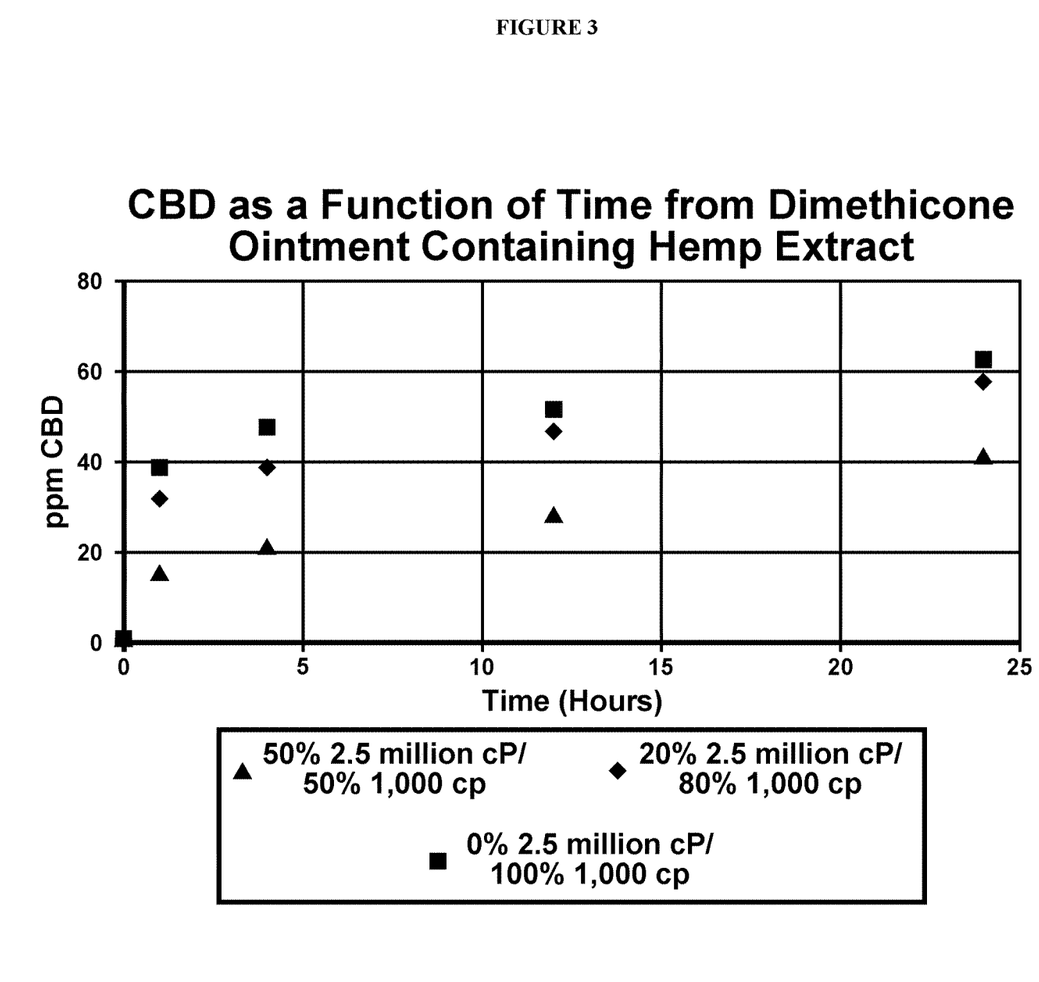
FIG. 3 depicts a release profile of several different blends of the present disclosure, with regard to release of CBD over a 24-hour period.

To confirm the release profile, a second active agent was tested to determine release profile as depicted in FIG. 3, namely the release of CBD from the material. FIG. 3 details a highly similar set of findings as compared to those of FIG. 2, namely that the lowest viscosity materials have a faster release profile, but that the total release profile is near identical to that of products that use a 4:1 ratio of low viscosity to high viscosity dimethicone. Indeed, while not depicted in the figures, fluoride release was also tested in an analogous study, and also confirmed the same general principals with regard to release. Thus, several different materials all show analogous and consistent release profiles from the material.

For purposes of a paste, gel, foam, liquid, aerosol, or food material, for application to a tooth surface, the oral mucosal carrier of the present disclosure must also have a profile that allows for application of the material at room temperature. Indeed, ease of application is necessary to ensure that the material is correctly applied, but also to aid in its ultimate use. A material that needs to be heated or chilled or applied with special applicators is likely to face burden from the professionals who will apply these materials, and thus the benefit of the product will remain in the drawer, unused, instead of on a tooth surface. Thus, the material, when in a paste, gel, or foam form is preferably a gel or paste like consistency which can be brushed or painted onto a tooth surface. When a liquid, it must be able to be swished in the mouth to coat, or when in an aerosol form, it must be able to be easily sprayed into the mouth for coating purpose. For a food material, one that maintains a form, or allows a coating over the material will be advantageous, Finally, the material, once in contact with the oral mucosa must adhere to the tooth and oral tissues, and then allow for saliva and the properties of the oral mucosa to allow for release of the excipients and therapeutics from the carrier.

The dimethicone carrier product of the present embodiments reduces many of the unwanted side effects of existing resin-based oral materials. Furthermore, these natural resins require an alcohol or other solvent for application and then leave a yellow or brown film on the tooth surface. This is realistically an aesthetic issue, but for children, adolescents, and adults who use such products, there is often a reluctance to maintain the product on tooth surfaces for the necessary duration to allow for the transfer of the fluoride to tooth surfaces. Thus, the material is rubbed off, by washing, brushing, flossing, or simply by tongue action. Indeed, existing resin-based oral products frequently suffer from a tactile feel on tooth surfaces that feels dirty, or grimy, and thus imparts tongue action to the tooth surfaces, which ultimately removes the oral mucosal carrier at an increased rate. The present embodiments comprise an oral mucosal carrier and protectant that has a clear color after application to the tooth surface and thus eliminates the brown or yellow coloration present in many of the resin-based materials.

Furthermore, the use of the dimethicone materials, provides for a smooth and clean tactile coating on tooth surfaces as well as the oral mucosal surfaces. Indeed, dimethicone products are frequently used for their ability to act as a lubricant or smooth texture. Thus, by creation of a smooth surface on the tooth and oral mucosal surfaces, there will be a reduction in tongue movement, and thus reduce the removal of the dimethicone-based formulations of the present disclosure as compared to those that rely upon natural resins as a carrier. By reducing the removal of the formulations, naturally there will be an increase in the time that the material is on the tooth or oral mucosal surfaces and thus an improvement of release of the materials to the tooth surface and oral mucosa.

A primary therapeutic agent component of the oral mucosal carrier may include fluoride. Fluoride comes in several different forms, but it is provided in the dimethicone carrier to be placed in close proximity to tooth surfaces and, when the oral mucosal carrier is applied to and adhered to (or adjacent to) a tooth surface, will impart remineralizing properties. For example, sodium fluoride is a common fluoride additive. Other fluorides known to those of skill in the art can also be utilized, for example stannous fluoride, ACPF, etc., are known and used in other oral care products. Each of these can be suitably added as a fluoride donor for remineralizing purposes.

Flavorant or sweeteners are frequently used in certain embodiments to provide for a pleasant taste when applying the material. In some embodiments described above, the tooth varnish compositions of the invention can further include one or more sweetening agents, flavoring agents, and coloring agents. Any suitable flavoring or sweetening material may be employed. Examples of suitable flavoring constituents includes natural or artificial tastes such as: natural flavorants, flavoring oils, e.g. including but not limited to: oil of spearmint, peppermint, wintergreen, clove, sage, eucalyptus, marjoram, cinnamon, citrus, vegetable, tree nut, fruit, and bramble. Other flavorants may include the oleoresin, essence or extractive, protein hydrolysate, distillate, or any product of roasting, heating or enzymolysis, which contain the flavoring constituents derived from a spice, fruit or fruit juice, vegetable or vegetable juice, edible yeast, herb, bark, bud, root, leaf or similar plant material, meat, seafood, poultry, eggs, dairy product, or fermentation products thereof, and other natural and synthetic flavoring agents as known to those of ordinary skill in the art.

Suitable sweetening agents include but are not limited to: nutritive and nonnutritive sweeteners, including sucrose, fructose, dextrose, high fructose corn syrup; sugar alcohols such as xylitol, maltitol, sorbitol, mannitol, erythritol; and artificial such as sucralose, aspartame, acesulfame potassium, saccharin, sedum saccharin and neotame; others may also include: lactose, maltose, sodium cyclamate, perillartine, AMP (aspartyl phenyl alanine methyl ester). Other natural and synthetic sweeting agents as known to those of ordinary skill in the art.

Suitably, flavor and/or sweetening agents may each or together comprise from up to 10%, or up to 5%, or up to 4%, or up to 3%, or up to 2%, or up to 1%, or from 0.5% to 1%, by weight of the composition. In certain embodiments, providing a material without a flavorant or sweetener might be preferable, however the material may then have little to no flavor and might cause concern to patients that the material is not on a tooth surface. Accordingly, a small amount of either the sweetener or flavorant may help the patient understand that the material is present.

A potential issue with the addition of a flavorant is that it may increase the rate of the material being washed away from the oral mucosal surfaces, and thus reduce the time the active ingredient or materials are present on the tooth or oral mucosal surfaces, including but not limited to the gums, tongue, cheeks, upper and lower portions of the mouth, and portions of the throat of the patient. While saliva flow is necessary in many cases to ensure application of the material to all oral surfaces, a rapid wash out of the material reduces the efficacy of the product. Therefore, the mucoadhesive properties of the dimethicone carrier are important to ensure that the material remains adjacent to the oral mucosa or tooth surfaces for a sufficient duration to allow for release of excipients or therapeutic agents.

Addition of a bulking agent or texture. As with the inclusion of a flavorant, it may be suitable to provide a small amount of a bulking agent or texturizing agent to the product to impart mass and substance, impart a tactile feel to the material, or to improve its consistency for application to the tooth surfaces. For example, addition of beeswax, other natural waxes, fats, oils, Gantrez® (synthetic, alternating copolymers of methyl vinyl ether [MVE] and maleic anhydride), and other agents that can modify the flow, texture, and viscosity of the finalized product. Other bulking agents may include mannitol, dicalcium phosphate, calcium sulfate, dry starch, cellulose, kaolin, sodium chloride, anhydrous lactose, sorbitol, sucrose, and the like. Those of ordinary skill in the art recognize that bulking agents are frequently used in formation of pharmaceutical and oral products and thus understand the meaning of term as used herein.

Additionally, a flowing agent may be added to modify the final physical properties of the material to impart greater or lesser viscosity, or the ability of the product to flow or remain in its targeted position upon contact with aqueous saliva in the mouth. For example, magnesium stearate, stearic acid, silicon dioxide, glycerin, palmitate, and others known to those of ordinary skill in the art. Those of ordinary skill in the art recognize that flowing agents are frequently used in formulation of pharmaceutical products and thus understand the meaning of the term as used herein.

Additional therapeutic materials may be suitably incorporated in the oral preparations of this invention such as whitening agents, including urea peroxide, calcium peroxide, titanium dioxide, hydrogen peroxide, complexes of polvinylpyridine (PVP) and hydrogen peroxide, preservatives, vitamins such as vitamin $B_6$, $B_{12}$, E, and K, silicones, chlorophyll compounds, potassium salts for the treatment of dental hypersensitivity such as potassium nitrate as well as antitartar agents such as sodium tripolyphosphate and di- and tetraalkali metal pyrophosphate salts such as di- and tetrasodium pyrophosphate, as well as calcium-based salts such as dicalcium phosphate, tricalcium phosphate, precipitated calcium carbonate either alone or in combination with amino acids such as L-arginine and L-lysine. These agents, when present, are incorporated in the compositions of the present invention in amounts which do not substantially adversely affect the properties and characteristics desired, and thus at typically added at between 0.1 and 10% weight percentage of the total composition.

Benzalkonium chloride may also be added as a therapeutic material, for its use as an antiseptic and disinfectant, and also for its preservative properties. However, when used in sufficient concentrations, its use as an antiseptic in the oral mucosa can help to reduce bacterial populations that may damage the oral mucosa. Other antibacterial agents may include, but are not limited to cetyl pyridinium chloride, trans-farnesol, chitosan, chlorhexidine, quaternary ammonium compounds, phenols, bisguanides, and combinations thereof.

Calcium nitrate, and other calcium donor materials can be used in conjunction with a fluoride ion donor. The goal of providing both a fluoride and a calcium donor is to allow for greater remineralizing to tooth surfaces. The carrier described herein is aqueous free. Unless a specific additive comprises water, the entire composition therefore is aqueous free.

In certain embodiments, it may also be suitable to add in a potassium donor, such as potassium phosphate dibasic or other potassium salts for tooth sensitivity treatments. Additional potassium donors, such as potassium nitrate, potassium chloride, and potassium phosphate monobasic are commonly utilized for combatting and reducing tooth sensitivity. Additionally, Arginine and lysine can be utilized for treating tooth sensitivity, as well as fluorides, oxalates, such as potassium oxalate, bioglass, ACP, or Casein-phosphopeptide-ACP, and other known materials.

In certain embodiments, it may be suitable to add in a phosphate donor, including those such as ACP, Casein-phosphopeptide-ACP, phosphate monobasic, potassium phosphate dibasic, dicalcium phosphate, tricalcium phosphate, sodium phosphate monobasic, sodium phosphate monobasic, sodium phosphate dibasic, monomagnesium phosphate, dimagnesium phosphate, and other donors as known to those of ordinary skill in the art, their salts, and combinations thereof.

The oral mucosal carrier and protectant material can be formulated under conditions that will prevent the growth of bacteria or prevent spoiling. Certainly, through inclusion of certain antibacterial agents, increased safety and an increased shelf life may be provided. The material can be formulated and then sterilized under ordinary procedures know to those of skill in the art in the field of oral care products. Alternatively, no sterilization process is necessary.

Xerostomia or dry mouth treatment may include pilocarpine, acetylcholine, electrolytes such as sodium, potassium, calcium, magnesium, chloride, phosphate, and carbonates. Saliva enhancers may be advantageously included in the mucosal carrier formulations of the present disclosure and include, for example: essential oil extracts, spilanthes, xylitol, carboxymethylcellulose and variations of the same to enhance saliva flow.

Halitosis treatment may include any number of the antibacterial compounds described herein, and/or natural or synthetic oils or odor destroying or odor masking agents.

Canker sore treatments are provided either without any additional compounds, as the carrier itself protects and coats canker sores, however additional excipients or therapeutic compounds may also be included. Alum powder (potassium aluminum sulfate), baking soda, probiotics, honey, coconut oils or other natural oil having antimicrobial properties, magnesium hydroxide, chamomile, echinacea, sage, deglycyrrhizinated licorice (DGL), zinc, Vitamin $B_{12}$, and other antimicrobial materials as described herein.

Dry Socket Treatment often comprises a pain medication as a first line of defense. For example, common NSAID or other pain medications, and other pain relieving materials including acetaminophen, or opioid-based materials. Additionally, an antibacterial or antimicrobial agent may be suitable. Additionally, an agent for tissue growth and healing may be suitable. For example, the following compounds are a nonlimiting list of possible additives: NSAID, opioid, acetaminophen, chlorhexidine, metronidazole, guaiacol, eugenol, balsam of Peru, chlorobutanol, iodoform, butamben, polymyxin B sulfate, tyrothricin, neomycin sulfate, tetracaine hydrochloride, and combinations thereof.

Peroxides (Whitening) may be suitable added as known to one of ordinary skill in the art. In certain cases, peroxides may also be used for their antibacterial and antimicrobial properties.

In particular embodiments herein comprise a portion of hemp extract. Hemp extract shall mean a material comprising a portion of extracted material from the hemp plant, containing at least one or more of certain cannabinoid or terpene molecules. Specifically, hemp extract is conceived to comprise one of either cannabidiol (CBD) or delta-9-tetrahydrocannabinol (THC). In certain embodiments, a low THC Hemp extract means one having less than 0.30% THC. A high THC Hemp extract means one comprising THC of more than 0.30% THC. Typically, hemp extracts are ethanol or $CO_2$ extracted from cannabis plants and comprise a plurality of cannabinoid and terpene molecules. These can be diluted with another carrier oil or solvent, as necessary.

Cannabinoids, including CBD and THC-infused topicals readily enter the skin layers only, however in the oral mucosa, there is opportunity for rapid uptake of the materials, thus providing an opportunity for increasing bioavailability through oral administration, but bypassing first-pass metabolism. Accordingly, the carrier materials defined herein are effective at delivering the cannabinoid compounds and other compounds to the body.

THC oral absorption is slow, with peak concentrations occurring 1-5 h postdose. THC bioavailability was 6% when orally administered, compared to up to 27% when inhaled. Plasma THC maximum concentrations were 4.4-11.0 µg/L after a 20 mg dose of oral THC. Once absorbed, THC is oxidized by the cytochrome P450 hepatic mixed function oxidase system to equipotent 11-hydroxy-THC (11-OH-THC), and further metabolized to inactive 11-nor-9-carboxy-THC (THCCOOH).

CBD has similar oral absorption and bioavailability to THC. Following doses of 10 mg CBD+10 mg THC in an oral capsule, mean (SD) peak plasma concentrations were 2.5 (2.2) µg/L CBD and 6.4 (3.1) µg/L THC, and after buccal Sativex (10 mg THC+10 mg CBD) were 3.0 (3.1) µg/L CBD and 6.1 (5.4) µg/L THC. Time to maximum concentration ($T_{max}$) was 1.3 (0.8) h for CBD and 1.0 (0.6) h for THC after oral administration, and 2.8 (1.3) h for CBD and 2.4 (1.1) h for THC after buccal administration.

Accordingly, new strategies to dispense cannabinoids orally is necessary, which is through adsorption through the oral mucosa. Within the mouth, there are three areas that absorb: the mucosa lining inside the entire mouth, the area under the tongue (sublingual) and the tongue itself. Cannabis products placed under the tongue (sublingually) take effect more quickly than those absorbed through the general mucosal tissue lining the mouth or placed on the tongue itself. With this uptake method, the effects of cannabis should be felt in 15-60 minutes. Accordingly, replacing oral dosing forms (through digestion) with a form for delivery to the oral mucosa is highly advantageous.

A primary use of these oral mucosal carrier and protectant materials is for delivery of the cannabinoid compounds, with ancillary benefits of any additional oral benefit. These might include remineralization to prevent or reduce caries, or for orthodontic bracket treatments, as previously described, may require some etching or damage to tooth enamel surfaces. Thus, after a bracket is adhered, treatment of the tooth surface would be advantageous to aid in remineralization and to prevent sensitivity or caries due to the weakening or removal of the enamel surface for the orthodontic application of brackets.

Methods of Manufacture of the Dimethicone Oral Mucosal Carrier Product

The mixture of two different viscosity dimethicone products, specifically of those having such a dramatic difference in viscosity provides significant hurdles in manufacturing and mixing of components. Indeed, one cannot simply add all of the components to a mixing bowl and mix/stir the components to create the instant formulations. Several different protocols were tested to allow for thorough mixture of the components until an appropriate process was generated.

As an example, the components of Example 1 below, were tested in several different mixing applications. Initially, all components were placed together in a single mixing vessel and mixed with a magnetic stirring rod. Mixture was impossible due to the viscosity of the material. A further test attempted to use a spinning/rotating mixing blade. However, the viscosity of the material made this difficult, except for the smallest amounts of the 2.5 million cP material, and the blades introduced significant amounts of air into the product making it unsuitable for use. After trial and error, a bladeless mixing system that utilizes centrifugal forces to aid in mixing, was found to be effective for mixing of the two different viscosity silicone materials and the additional excipients in the examples below.

EXAMPLES

Example 1

A Flacktek centrifugal mixer was used to mix the following compounds: dimethicone (2.5 million cP); dimethicone (1,000 cP); sodium fluoride. Initially, 17.6 grams of 1,000 cP dimethicone was added to the mixing cup. Next 0.02 grams of sodium fluoride was added to the mixing cup. The two compounds were mixed at 3,000 RPM for 10 minutes. Next 2.4 grams of the 2.5 million cP dimethicone was added in five increments of 0.48 grams. After each increment was added, the formulation was mixed for five-minute increments.

Subsequent formulation examples were prepared following the same procedure as Example 1. The following table lists the ratio of components used in the specific formulation example.

TABLE 1

| Formulation Example | Mass (g) of 1,000 cP Dimethicone | Mass (g) of 2.5 million cP Dimethicone | Mass (g) of Sodium Fluoride |
|---|---|---|---|
| 2 | 15.7 | 4.2 | 0.02 |
| 3 | 13.8 | 6.2 | 0.02 |
| 4 | 11.9 | 8.1 | 0.02 |
| 5 | 10.0 | 10.0 | 0.02 |

Example 6

A Flacktek mixer was used to mix the following compounds: dimethicone (2.5 million cP); dimethicone (12,500 cP); sodium fluoride. Initially, 17.6 grams of 12,500 cP dimethicone was added to the mixing cup. Next 0.02 gram of sodium fluoride was added to the mixing cup. The two compounds were mixed at 3,000 RPM for 10 minutes. Next 2.4 grams of the 2.5 million cP dimethicone was added in five increments of 0.48 grams. After each increment was added, the formulation was mixed for five-minute increments.

TABLE 2

| Formulation | Mass (g) of 12,500 cP Dimethicone | Mass (g) of 2.5 million cP Dimethicone | Mass (g) of Sodium Fluoride |
|---|---|---|---|
| 7 | 15.7 | 4.3 | 0.02 |
| 8 | 13.8 | 6.2 | 0.02 |
| 9 | 11.9 | 8.1 | 0.02 |
| 10 | 19 | 1 | 0.02 |
| 11 | 19.5 | 0.5 | 0.02 |

The mucoadhesion of the nine dimethicone oral mucosal formulations above were measured using the tensile test method as described in the literature. A Brookfield CT3 Texture Analyzer instrument was used at room temperature (23±1° C.). Twenty (20) grams of sample was used in a container and measurements were made within two minutes of filling the container. The Peak Adhesive Force was measured (n=6) for each formulation. These values are reported in Table 3 below. The Total Work of Adhesion was measured (n=6) for each oral mucosal formulation. These values are reported in Table 3 below. A larger negative number represents a greater adhesive force and a greater total work of adhesion.

TABLE 3

| Formulation | Peak Adhesive Force (N) | Total Work of Adhesion (N · sec) |
|---|---|---|
| 1 | −1.5 ± 0.03 | −0.68 ± 0.02 |
| 2 | −5.4 ± 0.15 | −2.0 ± 0.03 |
| 3 | −12.9 ± 1.2 | −5.3 ± 0.09 |
| 4 | −28.5 ± 2.7 | −10.8 ± 0.32 |
| 5 | −41.2 ± 1.7 | −16.5 ± 0.60 |
| 6 | −9.9 ± 0.33 | −3.7 ± 0.06 |
| 7 | −13.8 ± 0.28 | −6.6 ± 0.14 |
| 8 | −18.6 ± 1.7 | −10.9 ± 0.30 |
| 9 | −35.3 ± 4.0 | −16.0 ± 0.65 |

Example 10

Dimethicone Orthodontic Bracket Treatment Examples

A Flacktek mixer was used to mix the following compounds: dimethicone (2.5 million cP); dimethicone (1,000 cP); sodium fluoride. Initially, 15 grams of 1,000 cP dimethicone was added to the mixing cup. Next 20 milligrams of sodium fluoride were added to the mixing cup. The two compounds were mixed at 3,000 RPM for 10 minutes. Next 5 grams of the 2.5 million cP dimethicone was added in five increments of 1.0 grams. After each increment was added, the formulation was mixed for five-minute increments.

A Flacktek mixer was used to mix the following compounds: dimethicone (2.5 million cP); dimethicone (1,000 cP); sodium fluoride; calcium nitrate. Initially, 10 grams of 1,000 cP dimethicone was added to the mixing cup. Next 20 milligrams of sodium fluoride were added to the mixing cup. Then 20 milligrams of calcium nitrate were added to the mixing cup. The three compounds were mixed at 3,000 RPM for 10 minutes. Next 10 grams of the 2.5 million cP dimethicone was added in five increments of 2.0 grams. After each increment was added, the formulation was mixed for five-minute increments.

A Flacktek mixer was used to mix the following compounds: dimethicone (2.5 million cP); dimethicone (1,000 cP); sodium fluoride; calcium nitrate; potassium phosphate dibasic. Initially, 10 grams of 1,000 cP dimethicone was added to the mixing cup. Next 20 milligrams of sodium fluoride were added to the mixing cup. Then 20 milligrams of calcium nitrate were added to the mixing cup. Then 10 milligrams of potassium phosphate dibasic was added to the mixing cup. The four compounds were mixed at 3,000 RPM for 10 minutes. Next 10 grams of the 2.5 million cP dimethicone was added in five increments of 2.0 grams. After each increment was added, the formulation was mixed for five-minute increments.

A Flacktek mixer was used to mix the following compounds: dimethicone (2.5 million cP); dimethicone (1,000 cP); sodium fluoride; calcium nitrate; potassium phosphate dibasic, spearmint oil. Initially, 18 grams of 1,000 cP dimethicone was added to the mixing cup. Next 20 milligrams of sodium fluoride were added to the mixing cup. Then 20 milligrams of calcium nitrate were added to the mixing cup. Then 10 milligrams of potassium phosphate dibasic was added to the mixing cup. Next 80 milligrams of spearmint oil were added to the mixing cup. The five compounds were mixed at 3,000 RPM for 10 minutes. Next 2 grams of the 2.5 million cP dimethicone was added in five increments of 0.4 grams. After each increment was added, the formulation was mixed for five-minute increments.

A Flacktek mixer was used to mix the following compounds: dimethicone (2.5 million cP); dimethicone (1,000 cP); sodium fluoride; calcium nitrate; potassium phosphate dibasic, spearmint oil; cetylpyridinium chloride. Initially, 19 grams of 1,000 cP dimethicone was added to the mixing cup. Next 20 milligrams of sodium fluoride were added to the mixing cup. Then 20 milligrams of calcium nitrate were added to the mixing cup. Then 10 milligrams of potassium phosphate dibasic was added to the mixing cup. Next 80 milligrams of spearmint oil were added to the mixing cup. Then 100 milligrams of cetylpyridinium chloride was added to the mixing cup. The six compounds were mixed at 3,000 RPM for 10 minutes. Next 1 gram of the 2.5 million cP dimethicone was added in five increments of 0.2 grams. After each increment was added, the formulation was mixed for five-minute increments.

A Flacktek mixer was used to mix the following compounds: dimethicone (2.5 million cP); dimethicone (1,000 cP); stannous fluoride. Initially, 10 grams of 1,000 cP dimethicone was added to the mixing cup. Next 20 milligrams of stannous fluoride were added to the mixing cup. The two compounds were mixed at 3,000 RPM for 10 minutes. Next 10 grams of the 2.5 million cP dimethicone was added in five increments of 2.0 grams. After each increment was added, the formulation was mixed for 5 minute increments.

A Flacktek mixer was used to mix the following compounds: dimethicone (2.5 million cP); dimethicone (1,000 cP); stannous fluoride; calcium nitrate; potassium phosphate dibasic, spearmint oil; cetylpyridinium chloride. Initially, 19.5 grams of 1,000 cP dimethicone was added to the mixing cup. Next 20 milligrams of stannous fluoride were added to the mixing cup. Then 20 milligrams of calcium nitrate were added to the mixing cup. Then 10 milligrams of potassium phosphate dibasic was added to the mixing cup. Next 80 milligrams of spearmint oil were added to the mixing cup. Then 100 milligrams of cetylpyridinium chloride was added to the mixing cup. The six compounds were mixed at 3,000 RPM for 10 minutes. Next 0.5 grams of the 2.5 million cP dimethicone was added in two increments of 0.25 grams. After each increment was added, the formulation was mixed for five-minute increments.

Dimethicone Dry Mouth Treatment

A Flacktek mixer was used to mix the following compounds: dimethicone (2.5 million cP); dimethicone (1,000 cP); citric acid, sodium citrate, tartaric acid, sodium bicarbonate. Initially, 9.5 grams of 1,000 cP dimethicone was added to the mixing cup. Next, 0.5 grams of sodium bicarbonate was added to the mixing cup. Next 0.5 grams of tartaric acid was added to the mixing cup. Next 0.5 grams of citric acid was added to the mixing cup. Next, 0.5 grams of sodium citrate was added to the mixing cup. These five compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (12,500 cP). Initially, 9.5 grams of 12,500 cP dimethicone was added to the mixing cup. Next 9.5 grams of the 2.5 million cP dimethicone was added in five increments of 1.9 grams. After each increment was added, the formulation was mixed for five-minute increments. The mixture of two dimethicones together is a lubricating formulation.

A Flacktek mixer was used to mix the following compounds: dimethicone (2.5 million cP); dimethicone (1,000 cP); gentian; capsicum; statherin. Initially, 18.5 grams of 1,000 cP dimethicone was added to the mixing cup. Next, 0.2 grams of gentian was added to the mixing cup. Next 0.1 grams of capsicum was added to the mixing cup. Next 0.01 grams of statherin was added to the mixing cup. These four compounds were mixed at 3,000 RPM for 10 minutes. Next 0.5 grams of the 2.5 million cP dimethicone was added in five increments of 0.1 grams. After each increment was added, the formulation was mixed for five-minute increments.

Dimethicone Halitosis Delivery Examples

A Flacktek mixer was used to mix the following compounds: dimethicone (2.5 million cP); dimethicone (1,000 cP); peppermint oil. Initially, 10.1 grams of 1,000 cP dimethicone was added to the mixing cup. Next 0.04 grams of peppermint oil was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); cinnamon oil. Initially, 10.1 grams of 1,000 cP dimethicone was added to the mixing cup. Next 0.04 grams of cinnamon oil was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); wintergreen oil. Initially, 10.1 grams of 1,000 cP dimethicone was added to the mixing cup. Next 0.04 grams of wintergreen oil was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

Dimethicone Canker and Mouth Sore (Aphthous Ulcers, Herpetic, Stomatatic, Lichen Planus) Delivery Examples A Flacktek mixer was used to mix the following compounds: dimethicone (2.5 million cP); dimethicone (1,000 cP); fluocinonide. Initially, 10.1 grams of 1,000 cP dimethicone was added to the mixing cup. Next 50 milligrams of fluocinonide was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); benzocaine. Initially, 16.1 grams of 1,000 cP dimethicone was added to the mixing cup. Next 2 grams of benzocaine was added to the mixing cup. The two compounds were mixed at 3,000 RPM for 10 minutes. Next 3.5 grams of the 2.5 million cP dimethicone was added in three increments of 1.67 grams. After each increment was added, the formulation was mixed for five-minute increments.

A Flacktek mixer was used to mix the following compounds: dimethicone (2.5 million cP); dimethicone (12,500 cP); silver nitrate. Initially, 15.1 grams of 12,500 cP dimethicone was added to the mixing cup. Next 0.4 grams of silver nitrate was added to the mixing cup. The two compounds were mixed at 3,000 RPM for 10 minutes. Next 4.5 grams of the 2.5 million cP dimethicone was added in five increments of 0.9 grams. After each increment was added, the formulation was mixed for five-minute increments.

A Flacktek mixer was used to mix the following compounds: dimethicone (2.5 million cP); dimethicone (1,000 cP); triamcinolone; chlorhexidine; lidocaine. Initially, 18.1 grams of 1,000 cP dimethicone was added to the mixing cup. Next 0.1 grams of triamcinolone was added to the mixing cup. Next, 0.1 grams of chlorhexidine was added to the mixing cup. Next 1 gram of lidocaine was added to the mixing cup. The four compounds were mixed at 3,000 RPM for 10 minutes. Next 1.5 grams of the 2.5 million cP dimethicone was added in three increments of 0.5 grams. After each increment was added, the formulation was mixed for five-minute increments.

A Flacktek mixer was used to mix the following compounds: dimethicone (2.5 million cP); dimethicone (1,000 cP); fluocinonide; spearmint oil; chitosan. Initially, 10.1 grams of 1,000 cP dimethicone was added to the mixing cup. Next 50 milligrams of fluocinonide was added to the mixing cup. Next 40 milligrams of spearmint oil were added to the mixing cup. Next, 0.1 grams of chitosan was added to the mixing cup. The four compounds were mixed at 3,000 RPM for 10 minutes. Next 9.5 grams of the 2.5 million cP dimethicone was added in five increments of 1.9 grams. After each increment was added, the formulation was mixed for five-minute increments.

Dimethicone Dry Socket Treatment Delivery Examples

A Flacktek mixer was used to mix the following compounds: dimethicone (2.5 million cP); dimethicone (1,000 cP); acetaminophen; chlorhexidine; metronidazole. Initially, 19.1 grams of 1,000 cP dimethicone was added to the mixing cup. Next, 0.5 grams of ibuprofen was added to the mixing cup. Next, 0.1 grams of chlorhexidine was added to the mixing cup. Next, 0.5 grams of metronidazole was added to the mixing cup. The four compounds were mixed at 3,000 RPM for 10 minutes. Next 0.5 grams of the 2.5 million cP dimethicone was added in two increments of 0.25 grams. After each increment was added, the formulation was mixed for five-minute increments.

A Flacktek mixer was used to mix the following compounds: dimethicone (2.5 million cP); dimethicone (1,000 cP); guaiacol; eugenol; balsam of Peru; chlorobutanol. Initially, 10.1 grams of 1,000 cP dimethicone was added to the mixing cup. Next, 0.5 grams of ibuprofen was added to the mixing cup. Next, 1 gram of guaiacol was added to the mixing cup. Next, 0.4 grams of eugenol was added to the mixing cup. Next, 0.4 grams of chlorobutanol was added to the mixing cup. The five compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); iodoform; eugenol; butamben. Initially, 10.1 grams of 1,000 cP dimethicone was added to the mixing cup. Next, 0.4 grams of iodoform was added to the mixing cup. Next, 0.4 grams of eugenol was added to the mixing cup. Next, 0.8 grams of butamben was added to the mixing cup. The four compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); polymyxin B sulfate; tyrothricin; neomycin sulfate; tetracaine hydrochloride. Initially, 10.1 grams of 1,000 cP dimethicone was added to the mixing cup. Next, 0.5 grams of polymyxin B was added to the mixing cup. Next, 0.5 grams of tyrothricin was added to the mixing cup. Next, 0.5 grams of neomycin sulfate was added to the mixing cup. Next, 0.4 grams of tetracaine hydrochloride was added to the mixing cup. The five compounds were mixed at 3,000 RPM for 10 minutes. Next 9.5 grams of the 2.5 million cP dimethicone was added in five increments of 1.9 grams. After each increment was added, the formulation was mixed for five-minute increments.

Dimethicone Mucositis Treatment Delivery Examples

A Flacktek mixer was used to mix the following compounds: dimethicone (2.5 million cP); dimethicone (1,000 cP); chlorhexidine gluconate; lidocaine. Initially, 18.5 grams of 1,000 cP dimethicone was added to the mixing cup. Next 0.3 grams of chlorhexidine gluconate was added to the mixing cup. Next 1.5 grams of lidocaine was added to the mixing cup. The three compounds were mixed at 3,000 RPM for 10 minutes. Next 0.5 grams of the 2.5 million cP dimethicone was added in a single increment and the formulation was mixed for five-minutes.

A Flacktek mixer was used to mix the following compounds: dimethicone (2.5 million cP); dimethicone (1,000 cP); chlorhexidine gluconate; lidocaine; palifermin. Initially, 9.5 grams of 1,000 cP dimethicone was added to the mixing cup. Next 0.3 grams of chlorhexidine gluconate was added to the mixing cup. Next 1.5 grams of lidocaine was added to the mixing cup. Next 5 milligrams of palifermin was added to the mixing cup. The four compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); chlorhexidine gluconate; lidocaine; palifermin; potassium phosphate dibasic; calcium chloride. Initially, 9.5 grams of 1,000 cP dimethicone was added to the mixing cup. Next 0.3 grams of chlorhexidine gluconate was added to the mixing cup. Next 1.5 grams of lidocaine was added to the mixing cup. Next 5 milligrams of palifermin was added to the mixing cup. Next 0.5 grams of potassium phosphate dibasic was added to the mixing cup. Next 0.5 grams of calcium chloride was added to the mixing cup. The six compounds were mixed at 3,000 RPM for 10 minutes. Next 9.5 grams of the 2.5 million cP dimethicone was added in five increments of 1.9 grams. After each increment was added, the formulation was mixed for five-minute increments.

Dimethicone Whitening Treatment Delivery Examples

A Flacktek mixer was used to mix the following compounds: dimethicone (2.5 million cP); dimethicone (1,000 cP); carbamide peroxide. Initially, 9.5 grams of 1,000 cP dimethicone was added to the mixing cup. Next 1 gram of carbamide peroxide was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); carbamide peroxide; spearmint oil. Initially, 18.5 grams of 1,000 cP dimethicone was added to the mixing cup. Next 1 gram of carbamide peroxide was added to the mixing cup. Next, 40 milligrams of spearmint oil were added to the mixing cup. The three compounds were mixed at 3,000 RPM for 10 minutes. Next 0.5 grams of the 2.5 million cP dimethicone was added in five increments of 0.1 grams. After each increment was added, the formulation was mixed for 5 minute increments.

A Flacktek mixer was used to mix the following compounds: dimethicone (2.5 million cP); dimethicone (12,500 cP); carbamide peroxide; spearmint oil; potassium nitrate. Initially, 9.5 grams of 12,500 cP dimethicone was added to the mixing cup. Next 1 gram of carbamide peroxide was added to the mixing cup. Next, 40 milligrams of spearmint oil were added to the mixing cup. Next, 0.75 grams of potassium nitrate was added to the mixing cup. The four compounds were mixed at 3,000 RPM for 10 minutes. Next 9.5 grams of the 2.5 million cP dimethicone was added in five increments of 1.9 grams. After each increment was added, the formulation was mixed for five-minute increments.

Dimethicone Tooth Hypersensitivity Treatment Delivery Examples

A Flacktek mixer was used to mix the following compounds: dimethicone (2.5 million cP); dimethicone (1,000 cP); potassium nitrate. Initially, 9.5 grams of 1,000 cP dimethicone was added to the mixing cup. Next 1 gram of potassium nitrate was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); potassium nitrate; spearmint oil. Initially, 14.5 grams of 1,000 cP dimethicone was added to the mixing cup. Next 1 gram of potassium nitrate was added to the mixing cup. Next, 40 milligrams of spearmint oil were added to the mixing cup. The three compounds were mixed at 3,000 RPM for 10 minutes. Next 4.5 grams of the 2.5 million cP dimethicone was added in three increments of 1.5 grams. After each increment was added, the formulation was mixed for five-minute increments.

A Flacktek mixer was used to mix the following compounds: dimethicone (2.5 million cP); dimethicone (1,000 cP); potassium nitrate; spearmint oil; zinc chloride. Initially, 18.5 grams of 1,000 cP dimethicone was added to the mixing cup. Next 1 gram of potassium nitrate was added to the mixing cup. Next, 40 milligrams of spearmint oil were added to the mixing cup. Next 0.5 grams of zinc chloride was added to the mixing cup. The four compounds were mixed at 3,000 RPM for 10 minutes. Next 0.5 grams of the 2.5 million cP dimethicone was added in five increments of 0.1 grams. After each increment was added, the formulation was mixed for five-minute increments.

A Flacktek mixer was used to mix the following compounds: dimethicone (2.5 million cP); dimethicone (12,500 cP); potassium nitrate; spearmint oil; zinc chloride, calcium phosphate. Initially, 14.5 grams of 12,500 cP dimethicone was added to the mixing cup. Next 1 gram of potassium nitrate was added to the mixing cup. Next, 40 milligrams of spearmint oil were added to the mixing cup. Next 0.5 grams of zinc chloride was added to the mixing cup. Next 0.4 grams of calcium phosphate was added to the mixing cup. The five compounds were mixed at 3,000 RPM for 10 minutes. Next 4.5 grams of the 2.5 million cP dimethicone was added in five increments of 0.9 grams. After each increment was added, the formulation was mixed for five-minute increments.

A Flacktek mixer was used to mix the following compounds: dimethicone (2.5 million cP); dimethicone (25,000 cP); potassium nitrate; spearmint oil; zinc chloride, calcium phosphate; sodium fluoride. Initially, 9.5 grams of 25,000 cP dimethicone was added to the mixing cup. Next 1 gram of potassium nitrate was added to the mixing cup. Next, 40 milligrams of spearmint oil were added to the mixing cup. Next 0.5 grams of zinc chloride was added to the mixing cup. Next 0.4 grams of calcium phosphate was added to the mixing cup. Next 20 milligrams of sodium fluoride were added to the mixing cup. The six compounds were mixed at 3,000 RPM for 10 minutes. Next 9.5 grams of the 2.5 million cP dimethicone was added in five increments of 1.9 grams. After each increment was added, the formulation was mixed for five-minute increments.

Addition of CBD

Example 11: A Flacktek mixer was used to mix the following compounds: dimethicone (2.5 million cP); dimethicone (12,500 cP); hemp extract. Initially, 17.1 grams of 12,500 cP dimethicone was added to the mixing cup. Next 25 mg of CBD extract, via 1 mL of a nonaqueous hemp extract oil was added to the mixing cup. The two materials were mixed at 3,000 RPM for 10 minutes. Next 1.9 grams of the 2.5 million cP dimethicone was added in five increments of 0.38 grams. After each increment was added, the formulation was mixed for five-minute increments.

Subsequent formulation examples were prepared following the same procedure as Example 11. The following table lists the ratio of components used in the specific formulation example.

TABLE 4

| Formulation Example | Mass (g) of 1,000 cP Dimethicone | Mass (g) of 2.5 million cP Dimethicone | Mass (mg) of CBD |
|---|---|---|---|
| 12 | 15.2 | 3.8 | 25 |
| 13 | 13.3 | 5.7 | 25 |
| 14 | 11.4 | 7.6 | 25 |
| 15 | 9.5 | 9.5 | 25 |

Example 16

A Flacktek mixer was used to mix the following compounds: dimethicone (2.5 million cP); dimethicone (12,500 cP); CBD. Initially, 17.1 grams of 12,500 cP dimethicone was added to the mixing cup. Next 12.5 mg of benzalkonium chloride was added to the mixing cup. The two compounds were mixed at 3,000 RPM for 10 minutes. Next 1.9 grams of the 2.5 million cP dimethicone was added in five increments of 0.38 grams. After each increment was added, the formulation was mixed for five-minute increments.

TABLE 5

| Formulation | Mass (g) of 12,500 cP Dimethicone | Mass (g) of 2.5 million cP Dimethicone | Mass (mg) of CBD |
|---|---|---|---|
| 17 | 15.2 | 3.8 | 12.5 |
| 18 | 13.3 | 5.7 | 12.5 |
| 19 | 11.4 | 7.6 | 12.5 |

A Flacktek mixer was used to mix the following compounds: dimethicone (2.5 million cP); dimethicone (1,000 cP); 12.5 mg CBD, and Nystatin. Initially, 10.1 grams of 1,000 cP dimethicone was added to the mixing cup. Next 0.5 mL (12.5 mg of CBD) and 0.4 grams of Nystatin was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (12,500 cP); CBD, bacitracin; neomycin; polymyxin B. Initially, 18.5 grams of 12,500 cP dimethicone was added to the mixing cup. Next 12.5 mg CBD and 1.45 grams of bacitracin was added to the mixing cup. Next 70 mg of neomycin was added to the mixing cup. Next, 14 mg of polymyxin B was added to the mixing cup. The four compounds were mixed at 3,000 RPM for 10 minutes. Next 0.5 grams of the 2.5 million cP dimethicone was added in five increments of 0.1 grams. After each increment was added, the formulation was mixed for five-minute increments.

A Flacktek mixer was used to mix the following compounds: dimethicone (2.5 million cP); dimethicone (1,000 cP); CBD, tranexamic acid. Initially, 9.5 grams of 1,000 cP dimethicone was added to the mixing cup. Next 12.5 mg CBD and 1 gram of tranexamic acid was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (25,000 cP); CBD. Initially, 9.5 grams of 25,000 cP dimethicone was added to the mixing cup. Next 25 mg CBD was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

THC Delivery Formulation

A Flacktek mixer was used to mix the following compounds: dimethicone (2.5 million cP); dimethicone (12,500 cP); 25% THC. Initially, 9.5 grams of 1,000 cP dimethicone was added to the mixing cup. Next 25 mg of THC was added to the mixing cup, via 1 mL of an oil carrier comprising the THC. The two compounds were mixed at 3,000 RPM for 10 minutes. Next 9.5 grams of the 2.5 million cP dimethicone was added in five increments of 1.9 grams. After each increment was added, the formulation was mixed for five-minute increments. In preferred embodiments, the oil carrier is hemp oil, coconut oil, or a grain oil.

A Flacktek mixer was used to mix the following compounds: dimethicone (2.5 million cP); dimethicone (1,000 cP); spearmint oil; hemp extract. Initially, 9.5 grams of 1,000 cP dimethicone was added to the mixing cup. Next, 40 milligrams of spearmint oil were added to the mixing cup. Next 25 milligrams of CBD were added to the mixing cup. The compounds were mixed at 3,000 RPM for 10 minutes. Next 9.5 grams of the 2.5 million cP dimethicone was added in five increments of 1.9 grams. After each increment was added, the formulation was mixed for five-minute increments.

In certain embodiments, 5-25 mg of THC via a hemp extract was added to the combination and admixed therein.

In certain embodiments a different flavor oil may be admixed for the flavor.

A Flacktek mixer was used to mix the following compounds: dimethicone (2.5 million cP); dimethicone (1,000 cP); spearmint oil; hemp extract, a wax. Initially, 9.5 grams of 1,000 cP dimethicone was added to the mixing cup; 5 mg of wax, and 40 milligrams of spearmint oil was added to the mixing cup. Next 25 milligrams of CBD were added to the mixing cup. The compounds were mixed at 3,000 RPM for 10 minutes. Next 9.5 grams of the 2.5 million cP dimethicone was added in five increments of 1.9 grams. After each increment was added, the formulation was mixed for five-minute increments.

In a further embodiment the wax is a plant-based wax. In a further embodiment, the wax is beeswax in concentrations of 10 mg, 15, 20, and 25 mg were added to the mixture. In certain embodiments, THC was additionally included at concentrations of 5-25 mg.

Discussion

As we evaluated each of the formulations, a pattern arose that upon mixing of more of the high viscosity 2.5 million cP dimethicone into the formulations, the ability to work with the material eroded with regard to formulation of liquid, gel, paste, and foam materials with regard to spreading the material. However, as viscosity increased, with the increased amounts of the 2.5 million cP dimethicone, the formulation of food products increased, for example materials that incorporate a gelatin for formulation of a gummy like material, or formation of a solid or near solid material for oral treatment as a lozenge were able to be incorporated. For flowing materials, at a mixture of 100:1, 50:1, 40:1, 20:1, 10:1, 5:1; 1:1; 1:2; 1:5 and 1:8 were evaluated (1,000: 2.5 million cP) for their efficacy. Additional mixtures were also evaluated in various other examples.

However, at a sample of 1:1 ratio, of the 1,000 cP and 2.5 million cP dimethicone, the consistency and usability of the material was greatly reduced for liquid, gel, paste, or foam like applications. While at 1:1 ratio, the material would still be able to be applied to a tooth surface, it was not as workable, with regards to being applied in liquid form, as the lower ratio materials. However, inclusion of other excipients and even greater amounts of the 2.5 million cP dimethicone generated new materials, that are intended as food materials, (lollipop, lozenge, gummy, or the like, can be placed in the oral mucosa. Inundation with saliva in the oral mucosa allows for release of the components from within the carrier material. Thus, food materials, allow for coating and then release of the material in the same manner as a liquid, gel, or other application form.

Accordingly, variations in the amount of each of the first and second dimethicone products depended on the ultimate formulation, whether in a liquid, gel, paste, foam, or a gummy like or solid consistency. In certain preferred embodiments, the material can also be formulated into an aerosol and sprayed into the mouth for application. The aerosolized particles allow for quick, broad application to the oral mucosal surfaces.

In certain preferred embodiments, the oral mucosal carrier composition consisting essentially of: a dimethicone-based oral mucosal carrier comprising a first dimethicone material having a viscosity of between about 1,000 cP and 25,000 cP, and a second dimethicone material having a viscosity of between about 2.0 million and 3.0 million cP; and at least one active agent. In preferred embodiments, the first dimethicone to the second dimethicone is combined in a ratio of between 100:1 and 1:10, and preferably between 50:1 and 1:1. In preferred embodiments, the composition consisting essentially of at least one excipient.

In certain preferred embodiments, the oral mucosal carrier composition consisting of a dimethicone-based oral mucosal carrier comprising a first dimethicone material having a viscosity of between about 1,000 cP and 25,000 cP, and a second dimethicone material having a viscosity of between about 2.0 million and 3.0 million cP; and at least one active agent. In preferred embodiments, the first dimethicone to the second dimethicone is combined in a ratio between 100:1 and 1:10. In a preferred embodiment, the composition comprising two or more active agents. In a preferred embodiment, the composition comprising at least one excipient.

What is claimed is:

1. A dimethicone-based oral mucosal carrier comprising a first dimethicone material having a viscosity of between about 1,000 cP and 25,000 cP, and a second dimethicone material having a viscosity of between about 2.0 million and 3.0 million cP; and at least one active agent, wherein the ratio of the first dimethicone to the second dimethicone is between 100:1 and 1:10 wherein the concentration of the first dimethicone material is between 25% and 99% of the weight of the dimethicone-based oral mucosal carrier and the concentration of the second dimethicone material is between 1% and 50% of the weight of the dimethicone-based oral mucosal carrier.

2. The oral mucosal carrier of claim 1 wherein the active agent is selected from the group consisting of: a fluoride donor wherein the concentration of the fluoride donor is between 800 ppm and 1500 ppm, cetyl pyridinium chloride, benzalkonium chloride, and combinations thereof.

3. The oral mucosal carrier of claim 2 further comprising a calcium donor or a potassium donor.

4. The oral mucosal carrier of claim 1 further comprising a flavorant or a sweetener.

5. The oral mucosal carrier of claim 1 further comprising cetyl pyridinium chloride.

6. The oral mucosal carrier of claim 1 further comprising a bulking agent, a flowing agent, a preservative, or combinations thereof.

7. A method of formulating the oral mucosal carrier of claim 1 comprising placing a first dimethicone component into a mixing container and adding into it an amount of an active ingredient; mixing the first dimethicone component and the active ingredient at 3,000 RPM for a predetermined amount of time in a centrifugal mixer; and after mixing, adding to the now mixed material a first portion of a second dimethicone, wherein one fifth of the total concentration of the second dimethicone is added in separate increments and mixing the resulting material at 3,000 RPM for a predetermined period of time before adding another incremental portion of the second dimethicone, until all of the second dimethicone is added and admixed into the oral mucosal carrier wherein the concentration of the first dimethicone component is between 25% and 99% of the weight of the oral mucosal carrier and the concentration of the second dimethicone is between 1% and 50% of the weight of the oral mucosal carrier.

8. An oral mucosal carrier composition comprising: a dimethicone-based oral mucosal carrier comprising a first dimethicone material having a viscosity of between about 1,000 cP and 25,000 cP, and a second dimethicone material having a viscosity of between about 2.0 million and 3.0 million cP; and at least one active agent, wherein the ratio of the first dimethicone to the second dimethicone is between 100:1 and 1:10 wherein the concentration of the first dimethicone material is between 25% and 99% of the weight of the oral mucosal carrier composition and the concentration of the second dimethicone material is between 1% and 50% of the weight of the oral mucosal carrier composition.

9. The composition of claim 8 wherein the composition comprises two or more active agents.

10. The composition of claim 8 further comprising a bulking agent, wherein the bulking agent is selected from the group consisting of: an edible wax, a fat, an oil, mannitol, dicalcium phosphate, calcium sulfate, dry starch, cellulose, kaolin, anhydrous lactose, sorbitol, sucrose, and combinations thereof.

11. The composition of claim 10 wherein the bulking agent comprises between 0.01% and 15% of the total weight of the composition.

12. The composition of claim 8 wherein the active agent is a therapeutic agent selected from the group consisting of: sodium fluoride, difluorosilane, stannous fluoride, APF (acidulated phosphate fluoride), ACPF (amorphous calcium phosphate fluoride), ACP (amorphous calcium phosphate), sodium monofluorophosphate, benzalkonium chloride, potassium phosphate dibasic, calcium nitrate, cetylpyridinium chloride, phosphate donors, potassium donors, antibacterial, antifungal, antiviral, small molecules, antiemetic materials, biologic materials, self-replicating peptides, cannabinoids, terpenes, and combinations thereof.

13. The composition of claim 8 wherein the active agent is a hemp extract.

14. The composition of claim 8 wherein the active agent is a dry mouth treating agent selected from the group consisting of: pilocarpine, acetylcholine, electrolytes such as sodium, potassium, calcium, magnesium, chloride, phosphate, carbonates, and combinations thereof.

15. The composition of claim 8 wherein the active agent is a saliva enhancer selected from the group consisting of: essential oil extracts, spilanthes, xylitol, carboxymethylcellulose and variations of the same to enhance saliva flow.

16. The composition of claim 8 wherein the active agent is a halitosis treatment agent selected from the group consisting of: an antibacterial compound, a natural or synthetic oil, an odor destroying agent, and an odor masking agent.

17. The composition of claim 8 wherein the active agent is a canker sore treating agent selected from the group consisting of: alum powder (potassium aluminum sulfate), baking soda, probiotics, honey, coconut oils or other natural oil having antimicrobial properties, magnesium hydroxide, chamomile, echinacea, sage, deglycyrrhizinated licorice (DGL), zinc, vitamin B12, antimicrobial compounds, and combinations thereof.

18. The composition of claim 8 wherein the active agent is a dry socket treatment agent selected from the group consisting of: a pain relief agent, an antibacterial agent, and a tissue growth agent.

19. The composition of claim 18 wherein the active agent is selected from the group consisting of: NSAID, opioid, acetaminophen, chlorhexidine, metronidazole, guaiacol, eugenol, balsam of Peru, chlorobutanol, iodoform, butamben, polymyxin B sulfate, tyrothricin, neomycin sulfate, tetracaine hydrochloride, and combinations thereof.

20. The composition of claim 8 wherein the active agent is a peroxide.

* * * * *